US009873655B2

(12) United States Patent
Hallinan et al.

(10) Patent No.: US 9,873,655 B2
(45) Date of Patent: *Jan. 23, 2018

(54) SELECTIVE REMOVAL OF IMPURITIES IN ACETIC ACID PRODUCTION PROCESSES

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US); Brian A. Salisbury, Beach City, TX (US); John D. Hearn, Beach City, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,999

(22) Filed: Dec. 2, 2016

(65) Prior Publication Data

US 2017/0158596 A1 Jun. 8, 2017

Related U.S. Application Data

(60) Provisional application No. 62/262,654, filed on Dec. 3, 2015.

(51) Int. Cl.
- *C07C 51/12* (2006.01)
- *C07C 51/47* (2006.01)
- *B01D 15/08* (2006.01)
- *B01J 20/16* (2006.01)

(52) U.S. Cl.
CPC .............. *C07C 51/47* (2013.01); *B01D 15/08* (2013.01); *B01J 20/16* (2013.01); *C07C 51/12* (2013.01)

(58) Field of Classification Search
CPC ......... C07C 53/08; C07C 51/12; C07C 51/47; B01D 15/08; B01J 20/16
See application file for complete search history.

(56) References Cited

U.S. PATENT DOCUMENTS

| 4,701,562 A | 10/1987 | Olson |
| 4,704,478 A | 11/1987 | Olson |
| 7,332,636 B2 * | 2/2008 | Xu .................. B01J 29/06 585/638 |
| 7,345,197 B1 | 3/2008 | Hallinan et al. |
| 7,390,919 B1 | 6/2008 | Salisbury et al. |
| 8,017,802 B2 | 9/2011 | Scates et al. |
| 8,076,512 B2 | 12/2011 | Fitzpatrick et al. |
| 8,114,671 B2 | 2/2012 | Hallinan |
| 8,293,534 B2 | 10/2012 | Hallinan |
| 8,969,613 B2 | 3/2015 | Hallinan et al. |
| 2008/0293967 A1 * | 11/2008 | Scates .................. C07C 51/12 562/517 |
| 2016/0121320 A1 | 5/2016 | You et al. |

FOREIGN PATENT DOCUMENTS

| EP | 2594547 | * | 5/2013 |
| WO | WO-2008016502 A2 | | 2/2008 |
| WO | WO2014/070739 | * | 5/2014 |
| WO | WO-2014070739 A1 | | 5/2014 |
| WO | WO-2014199593 A1 | | 12/2014 |

OTHER PUBLICATIONS

Dumitriu et al, Microporous Materials, 10, pp. 1-12, 1997.
Weili Dai et al, Methanol-to-Olefin Conversion on Silicoaluminophosphate Catalysts: Effect of Bronsted Acid Sites and Framework Structures, ACS Catalysis, vol. 1, No. 4, Apr. 1, 2011, pp. 292-299, XP55279825.
The International Search Report and Written Opinion for PCT/US2016/064731 dated Feb. 23, 2017.

* cited by examiner

*Primary Examiner* — Yevgeny Valenrod
*Assistant Examiner* — Blaine G Doletski (57) ABSTRACT

Processes for producing carboxylic acid are included herein. The processes include contacting methanol and carbon monoxide in the presence of a liquid reaction medium under carbonylation conditions sufficient to form a carbonylation product including acetic acid and one or more components selected from acetaldehyde, formic acid and combinations thereof, wherein the liquid reaction medium includes: a carbonylation catalyst selected from rhodium catalysts, iridium catalysts and palladium catalysts; and water in a water concentration in a range of 1 wt. % to 14 wt. % based on the total weight of the liquid reaction medium; and contacting at least a portion of the carbonylation product or a derivative thereof with an adsorbent at adsorption conditions sufficient to selectively reduce a concentration of one or more components present in the carbonylation product, wherein the adsorbent includes a silicoaluminophosphate (SAPO).

19 Claims, 10 Drawing Sheets

SELECTIVE REMOVAL OF IMPURITIES IN ACETIC ACID PRODUCTION PROCESSES

CROSS-REFERENCE TO RELATED APPLICATIONS

This application claims the benefit of priority to U.S. Provisional Application No. 62/262,654, filed on Dec. 3, 2015, which is incorporated herein by reference in its entirety.

FIELD OF THE INVENTION

The present disclosure relates to the production of acetic acid and related processes. In particular, embodiments contained herein relate to selective removal of impurities within such processes.

BACKGROUND OF THE INVENTION

This section introduces information from the art that may be related to or provide context for some aspects of the techniques described herein and/or claimed below. This information is background facilitating a better understanding of that which is disclosed herein. Such background may include a discussion of "related" art. That such art is related in no way implies that it is also "prior" art.

Carboxylic acids, such as acetic acid, may be commercially produced by alcohol carbonylation. Unfortunately, carbonylation processes often create unwanted by-products. Significant energy has been devoted to the removal of such by-products, including a variety of processes and techniques. However, such processes and techniques can be difficult and costly.

Contained herein are embodiments directed to resolving, or at least reducing, one or all of the problems mentioned above.

SUMMARY OF THE INVENTION

The present disclosure relates to the production of acetic acid and related processes. In some embodiments, the processes include contacting methanol and carbon monoxide in the presence of a liquid reaction medium under carbonylation conditions sufficient to form a carbonylation product including acetic acid and one or more components selected from acetaldehyde, formic acid and combinations thereof, wherein the liquid reaction medium includes: a carbonylation catalyst selected from rhodium catalysts, iridium catalysts and palladium catalysts; water in a concentration range of 1 wt. % to 14 wt. % based on the total weight of the liquid reaction medium; and contacting at least a portion of the carbonylation product or a derivative thereof with an adsorbent at adsorption conditions sufficient to selectively reduce a concentration of one or more components present in the carbonylation product, wherein the adsorbent includes a silicoaluminophosphate (SAPO).

One or more embodiments include the process of the preceding paragraph, wherein the adsorbent is represented by the formula $(SiO_2)_x(Al_2O_3)_y(P_2O_5)_z$.

One or more embodiments include the process of any preceding paragraph, wherein the adsorbent comprises a micro-porous material.

One or more embodiments include the process of any preceding paragraph, wherein the adsorbent includes an average surface area of at least 500 meters $(m)^2$/gram (g).

One or more embodiments include the process of any preceding paragraph, wherein the adsorbent includes an average pore volume of at least 0.23 centimeters $(cm)^3$/g.

One or more embodiments include the process of any preceding paragraph, wherein the adsorbent is disposed on a fixed bed and the at least a portion of the carbonylation product stream passes through the bed to selectively reduce the concentration of the one or more components.

One or more embodiments include the process of any preceding paragraph, wherein the adsorbent is loaded on the fixed bed at a level sufficient to provide a loading of from 1 to 10 g adsorbent/g component to be selectively adsorbed.

One or more embodiments include the process of any preceding paragraph, wherein the adsorption conditions include an adsorption temperature in a range of room temperature, e.g. about 20 to 28° C., to 250° C.

One or more embodiments include the process of any preceding paragraph, wherein the at least a portion of the carbonylation product includes acetaldehyde, formic acid or a combination thereof and less than 1 wt. % water.

One or more embodiments include the process of any preceding paragraph, wherein a concentration of acetaldehyde is selectively reduced by at least 80%.

One or more embodiments include the process of any preceding paragraph, wherein acetaldehyde is selectively reduced to provide a purified acetic acid stream including an acetaldehyde concentration of less than 2 wt. % based on the total weight of the purified acetic acid stream.

One or more embodiments include the process of any preceding paragraph, wherein a concentration of formic acid is selectively reduced by at least 80%.

One or more embodiments include the process of any preceding paragraph, wherein formic acid is selectively reduced to provide a purified acetic acid stream including a formic acid concentration of less than 2 wt. % based on the total weight of the purified acetic acid stream.

One or more embodiments include the process of any preceding paragraph, wherein the at least a portion of the carbonylation product includes water at a concentration of at least 200 ppm based on the total weight of the carbonylation product.

One or more embodiments include the process of any preceding paragraph, wherein the concentration of water present in the at least a portion of the carbonylation product stream is selectively reduced by at least 50%.

One or more embodiments include the process of any preceding paragraph, wherein water is selectively reduced to provide a purified acetic acid stream including a water concentration of less than 1 wt. % based on the total weight of the purified acetic acid stream.

One or more embodiments include the process of any preceding paragraph, wherein the adsorbent includes a three-dimensional framework of cages interconnected by windows.

One or more embodiments include the process of any preceding paragraph, wherein the adsorbent includes an average cage diameter in a range of 4 angstroms (Å) to 12 angstroms.

One or more embodiments include the process of any preceding paragraph, wherein the adsorbent includes an average window diameter in a range of 2 angstroms to 6 angstroms.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the drawings and detailed description are to be regarded as illustrative in nature and not restrictive.

BRIEF DESCRIPTION OF THE DRAWINGS

The claimed subject matter may be understood by referring to the following description and figures, in which identical numerals correspond to identical elements, and in which:

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover modifications, equivalents, and alternatives falling within the spirit and scope as defined by the appended claims.

DETAILED DESCRIPTION OF THE INVENTION

Illustrative embodiments of the subject matter claimed below will now be disclosed. In the interest of clarity, not all features of an actual implementation are described in this specification. It will be appreciated that in the development of any such actual embodiment, numerous implementation-specific decisions can be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range.

Further, in the description below, unless otherwise specified, the compounds described herein may be substituted or unsubstituted and the listing of compounds includes derivatives thereof.

Embodiments described herein include processes for producing acetic acid. Furthermore, one or more specific embodiments include production of glacial acetic acid (which is encompassed by the term "acetic acid" as referenced herein). Glacial acetic acid refers to acetic acid that is often undiluted (includes a water concentration of up to about 0.15 wt. % based on the total weight of acetic acid and water). In one or more embodiments, the acetic acid production processes may include carbonylation processes. For example (and for purposes of discussion herein), the acetic acid production processes may include the carbonylation of methanol and/or its derivatives to produce acetic acid.

The carbonylation processes utilized to produce acetic acid often include reacting an alcohol, such as methanol, with carbon monoxide in the presence of a reaction medium, such as a liquid reaction medium, under carbonylation conditions sufficient to form a carbonylation product including acetic acid and recovering the formed acetic acid from the carbonylation product. As described herein, the term "liquid reaction medium" refers to a reaction medium that is primarily liquid in form. For example, the liquid reaction medium contains minor amounts of alternative phases. In one or more embodiments, the liquid reaction medium is at least 90%, or at least 91%, or at least 92%, or at least 93%, or at least 94%, or at least 95%, or at least 96%, or at least 97%, or at least 98%, or at least 99% liquid phase.

The reaction medium often includes a carbonylation catalyst. Carbonylation catalysts may include, but are not limited to, rhodium catalysts, iridium catalysts and palladium catalysts. Rhodium catalysts may include rhodium metal and rhodium compounds selected from rhodium salts, rhodium oxides, rhodium acetates, rhodium phosphates, organo-rhodium compounds, coordination compounds of rhodium and mixtures thereof (see, U.S. Pat. No. 5,817,869, which is incorporated in its entirety herein). Iridium catalysts may include iridium metal and iridium compounds selected from iridium acetates, iridium oxalates, iridium acetoacetates and mixtures thereof (see, U.S. Pat. No. 5,932,764, which is incorporated in its entirety herein).

The concentration of carbonylation catalyst in the reaction medium may be at least 7.5 millimolar (mmol) or may be in a range of 1 mmol to 100 mmol, or 2 mmol to 5 mmol, or 2 mmol to 75 mmol, or 5 mmol to 50 mmol, or 7.5 mmol to 25 mmol of catalyst per liter of reaction medium.

In one or more embodiments, the carbonylation catalyst is utilized with a co-catalyst. The co-catalyst may be selected from metals and metal compounds including osmium, rhenium, ruthenium, cadmium, mercury, zinc, gallium, indium, tungsten and mixtures thereof. In one or more embodiments, the metal compounds include metal acetates. The concentration of co-catalyst in the reaction medium may be in a range of 500 ppm to 3000 ppm, or 1000 ppm to 2000 ppm, based on the total reaction medium weight.

In one or more embodiments, the reaction medium further includes water. The concentration of water in the reaction medium may be in a range of 1 wt. % to 14 wt. %, or 10 wt.

% or less, or 8 wt. % or less, or 6 wt. % or less, or 1 wt. % to 5 wt. %, or 4 wt. % to 8 wt. % based on the total weight of the reaction medium.

The reaction medium may include an alkyl acetate, such as methyl acetate, for example. The concentration of alkyl acetate in the reaction medium may be in a range of 0.6 wt. % to 36 wt. %, or 2 wt. % to 20 wt. %, or 2 wt. % to 16 wt. %, or 3 wt. % to 10 wt. %, or 2 wt. % to 8 wt. % based on the total reaction medium weight.

In addition, it is contemplated that a supplemental gas such as hydrogen may be supplied to the reaction medium. Supplemental hydrogen may be supplied to the reaction medium to provide a total hydrogen concentration in the gaseous component of the feedstock to the carbonylation reaction in a range of 0.1 mol. % to 5 mol. %, or 0.3 mol. % to 3 mol. %.

In one or more embodiments, the reaction medium further includes one or more promoters. For example, the reaction medium may include an iodide promoter. The iodide promoter may include an alkyl iodide such as methyl iodide. The concentration of such promoters in the reaction medium may be in a range of 0.6 wt. % to 36 wt. %, or 4 wt. % to 24 wt. %, or 6 wt. % to 20 wt. % based on the total weight of the reaction medium. The iodide promoter may be introduced to the reaction medium in a form such that the introduced compound will directly promote the carbonylation reaction (e.g., introduction of methyl iodide to the carbonylation reaction). Alternatively, one or more compounds may be introduced to the reaction medium to form in-situ generated compounds capable of promoting the carbonylation reaction. For example, carbonylation processes may introduce hydrogen iodide to the reaction medium and form methyl iodide, which acts as a promoter.

In practice, carbonylation reaction conditions vary depending upon reaction parameters, reactor size and charge and the individual components employed. However, in one or more embodiments, the carbonylation process may be a batch or continuous processes and the carbonylation conditions may include a carbonylation pressure in a range of 200 pounds per square inch gage (psig) (1379 kilopascals (kPa)) to 2000 psig (13790 kPa), or 200 psig (1379 kPa) to 1000 psig (6895 kPa), or 300 psig (2068 kPa) to 500 psig (3447 kPa), and a carbonylation temperature in a range of 150° C. to 250° C., or 170° C. to 220° C., or 150° C. to 200° C.

In some embodiments, the carbonylation product includes the formed acetic acid. In addition to the acetic acid, the carbonylation product often includes one or more impurities. Impurities are defined herein as any component in a process stream other than the targeted product itself (e.g., acetic acid is the targeted product in the carbonylation product stream). For example, the impurities present in carbonylation product stream may include water, aldehydes (e.g., acetaldehyde, crotonaldehyde, butyraldehyde and derivatives thereof), alkanes, formic acid, methyl formate or combinations thereof as well as additional compounds other than the acetic acid, depending on the specific process.

The separation of impurities from the acetic acid prior to use of the acetic acid in subsequent processes such as industrial processes is often preferred or necessary. Such separation processes may include those available in the relevant literature and may include separating one or more of the impurities from the acetic acid within a process stream (wherein the process stream may be referred to as "impure acetic acid") to form purified acetic acid via one or more methods, including, but not limited to, extraction, distillation, extractive distillation, caustic treatment, scavenging, adsorption and combinations thereof. As used herein, the term "purified acetic acid" refers to an acetic acid stream having a concentration of one or more impurities that is reduced in comparison to that impurity's concentration in the impure acetic acid. It is to be noted that use of the term "acetic acid stream" herein refers to any stream containing acetic acid.

While many processes exist for the separation of the impurities, such processes can be difficult to implement, are not effective, and/or are costly. Thus, continuous efforts have been underway to improve and develop methods to separate these impurities from acetic acid. Embodiments described herein provide separation of one or more impurities via selective adsorption.

Thus, one or more embodiments include contacting at least a portion of the carbonylation product (or a derivative thereof) with an adsorbent at adsorption conditions sufficient to selectively reduce the concentration of one or more impurities present in the carbonylation product. As used herein, the term "selectively reduce" refers to the reduction in concentration of one or more target components (i.e., impurities) without substantial reduction in the concentration of acetic acid present in the stream. As used herein, the term "substantial" references a value that does not change by more than 0.5%.

In one or more embodiments, the impure acetic acid stream may include acetaldehyde at a concentration in a range of 0 wt. % to 4.5 wt. %, or at least 3 wt. %, or 2.5 wt. % to 3.5 wt. % based on the total weight of the impure acetic acid stream. The impure acetic acid stream may include formic acid at a concentration in a range of 0 wt. % to 4.5 wt. %, or at least 3 wt. %, or 2.5 wt. % to 3.5 wt. % based on the total weight of the impure acetic acid stream. In one or more specific, non-limiting embodiments, the impure acetic acid stream may include water at a concentration in a range of 0 wt. % to 2.5 wt. %, or at least 1.25 wt. %, or 1.25 wt. % to 2 wt. % based on the total weight of the impure acetic acid stream.

At least a portion of the carbonylation product contacts the adsorbent under adsorption conditions sufficient to selectively reduce the concentration of one or more components present in the carbonylation product. For example, the concentration of one or more of the impurities may be reduced by at least 50%, or at least 80%, or at least 85%, or at least 90%, or at least 95%, or at least 98%. In some embodiments, the purified acetic acid stream may include acetaldehyde at a concentration of less than 2 wt. %, or less than 1.5 wt. %, or less than 1 wt. % based on the total weight of the purified acetic acid stream. In certain embodiments, the purified acetic acid stream may include formic acid at a concentration of less than 2 wt. %, or less than 1.5 wt. %, or less than 1 wt. % based on the total weight of the purified acetic acid stream. In further embodiments, the purified acetic acid stream may include water at a concentration of less than 1 wt. %, or less than 0.75 wt. %, or less than 0.5 wt. % based on the total weight of the purified acetic acid stream.

The adsorbent often includes a micro-porous material. The term "micro-porous" as used herein refers to a material having an average pore diameter of less than 2 nanometers (nm). Microporous materials are typically composed of a structure of cavities (i.e., "cages") interconnected by smaller windows. The cage sizes are such that molecules can be accommodated and windows to the cages are often smaller than the actual cage. Accordingly, molecules that fit into the cage are not necessarily able to cross a window. In one or more embodiments, the adsorbents may have an average cage diameter in a range of 4 angstroms to 12 angstroms, or 6 angstroms to 10 angstroms, or 8 angstroms to 9.6 angstroms. The adsorbents may have an average window diameter in a range of 2 angstroms to 6 angstroms, or 3 angstroms to 5 angstroms, or 3.5 angstroms to 4 angstroms.

In one or more embodiments, the adsorbent includes a silicoaluminophosphate (SAPO). The SAPO may be represented by the general formula $(SiO_2)_x(Al_2O_3)_y(P_2O_5)_z$, wherein x, y and z are measured and defined as mole fractions of the metal atom and thus definition of x, y and z is in terms of the following formula: $(Si_xAl_yP_z)O_2$, where x+y+z=1. During preparation of the SAPO, Si is substituted into an aluminophsophate framework and thus, in the resultant SAPO, y may be about 0.5 and x+z may be about 0.5, for example. Further examples of measurement of x, y and z can be found in "New Developments in Zeolite Science and Technology", *React. Kinet. Catal. Lett.* 67 (2), 365-370 (1999), which is incorporated herein by reference.

As utilized herein, the silicoaluminophosphate (SAPO) materials include those having a three-dimensional framework of cages and windows. As used herein, the term "three-dimensional" refers to a structure arranged along three Cartesian axes, thus providing three-dimensional connectivity between cages and windows.

The SAPO materials may have a average surface area of at least 550 $m^2/g$, or at least 500 $m^2/g$, or at least 400 $m^2/g$. The SAPO materials may further have an average pore volume of at least 0.27 $cm^3/g$, or at least 0.23 $cm^3/g$, or at least 0.2 $cm^3/g$.

A variety of silicoaluminophosphates are commercially available, including, but not limited to SAPO-34, SAPO-11, SAPO-5, SAPO-18 and SAPO-21, for example. However, as demonstrated by the EXAMPLES included herein, not all commercially available SAPO materials are capable of selective adsorption as recited herein. In one or more embodiments, the adsorbent is SAPO-34, having an average cage diameter of 9.4 angstroms and an average window diameter of 3.8 angstroms.

At least a portion of the carbonylation product may contact the adsorbent via methods available in the relevant literature. For example, the adsorbent may be disposed on a fixed bed and the at least a portion of the carbonylation product may pass through the bed to selectively reduce the concentration of one or more components therein. The adsorbent may be disposed on the fixed bed by manners available in the relevant literature. The adsorbent may be loaded on the bed in an amount in a range of 1 g to 10 g adsorbent/g organic material to be adsorbed, or 2 g to 8 g adsorbent/g organic material to be adsorbed, or 4 g to 6 g adsorbent/g organic material to be adsorbed.

The adsorption conditions vary depending upon numerous factors. However, the adsorbent conditions are such that they promote adsorption but are not sufficient to promote catalysis/reaction. Thus, in one or more embodiments, the adsorption temperature is in a range of room temperature to 250° C., or room temperature to 225° C., or room temperature to 200° C. As used herein, "room temperature" means that a temperature difference of a few degrees does not matter to the phenomenon under investigation. In some environments, room temperature may include a temperature in a range of about 20° C. to about 28° C., while in other environments, room temperature may include a temperature in a range of about 10° C. to about 32° C., for example. However, room temperature measurements often do not include close monitoring of the temperature of the process and therefore such a recitation does not intend to bind the embodiments described herein to any predetermined temperature range.

It is contemplated that the adsorbent may occasionally require regeneration or replacement. The regeneration procedure often includes processing the spent adsorbent at room temperature or at high temperatures and may include any regeneration procedure available in the relevant literature. The adsorbent may be regenerated either in the adsorbent bed or may be removed from the adsorbent bed for regeneration. Such regeneration is known to the skilled artisan. However, a non-limiting illustrative embodiment of in-line regeneration is described below.

In a non-limiting example of in-line regeneration, the adsorbent bed is initially taken off-line and the adsorbent disposed therein is purged. Off-stream reactor purging may be performed by contacting the adsorbent in the off-line adsorbent bed with a purging stream, which may include an inert gas, e.g., nitrogen. The off-stream reactor purging conditions are typically determined by individual process parameters and are generally known to one skilled in the art.

The adsorbent may then optionally undergo a regeneration step. The regeneration conditions may be any conditions that are effective for at least partially reactivating the adsorbent and are generally known to one skilled in the art. For example, regeneration may include heating the adsorbent to a temperature or a series of temperatures, such as a regeneration temperature in a range of 50° C. to 200° C. above the adsorption temperature.

In order to minimize disruption to the process during periods of regeneration or replacement, one or more embodiments of the present disclosure utilize swing beds for the adsorption of one or more acetic acid processing impurities. In such embodiments, continuous operation can be achieved. For example, one adsorbent bed may be taken off-line for potential removal and/or regeneration of the adsorbent, while the remaining adsorbent bed may remain on-line for production.

In one or more embodiments, components within the carbonylation product stream (or at least a portion thereof) may be separated from one another via flash separation into a liquid fraction and a vapor fraction. The liquid fraction may include residual carbonylation catalyst as well as other components, while the vapor fraction may include acetic acid, unreacted reactants, water, methyl iodide and impurities generated during the carbonylation reaction. The liquid fraction may be recycled to the carbonylation reaction while the vapor fraction may undergo supplemental separation.

The supplemental separation may include a first column (e.g., a light ends distillation column) adapted to separate components of the liquid fraction and form a first overhead stream and an acetic acid stream. The first overhead stream may include methyl iodide, water, methanol, methyl acetate, impurities or combinations thereof, for example. The acetic acid stream may be passed to a drying column to remove any water contained therein and then a second column (e.g., a heavy ends distillation column) adapted to separate components of the acetic acid stream and form a second overhead stream and a bottoms stream. The second overhead stream may include methyl iodide, methyl acetate, acetic acid, water, impurities or combinations thereof.

The first overhead stream may be condensed and separated in a decanter to form, relative to each phase, a "light" aqueous phase and a "heavy" organic phase. The heavy organic phase may include methyl iodide and aldehyde impurities. The light aqueous phase may include water, acetic acid and methyl acetate. The light aqueous phase may be recycled to the reactor or for light ends distillation.

Any stream (or portion thereof) containing target impurities may contact the adsorbent to selectively reduce such impurities. However, one or more embodiments include contacting the acetic acid stream with the adsorbent. Alternative embodiments include contacting the second overhead stream with the adsorbent. Additional embodiments include contacting the heavy organic phase with the adsorbent.

Figure 1:
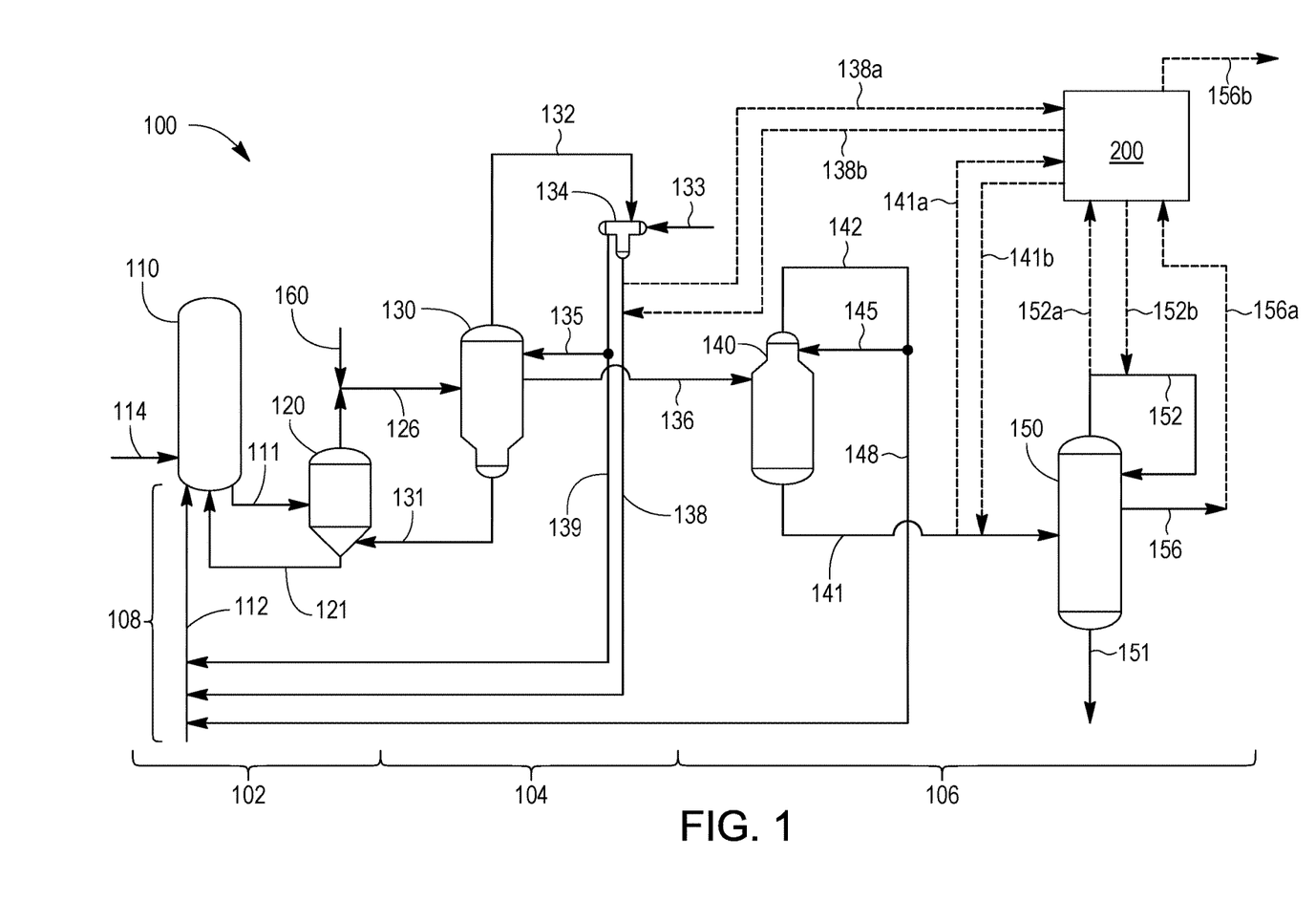
FIG. 1 illustrates a schematic of one or more embodiments of the disclosed processes.

FIG. 1 illustrates a schematic of an embodiment of a specific, non-limiting embodiment of a carboxylic acid production process 100. The process 100 may be described in terms of functional areas, i.e., a reaction area 102, a light-ends area 104, a purification area 106 and a recycle area 108, which correlate to specific processing equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and the flash vessel 120. For example, the reaction area 102 may include the reactor 110, the flash vessel 120, and streams (or portions of streams) 111, 112, 114, 121, 126, 131, 160, 138, 139 and 148. The reactor 110 is a reactor or vessel in which an alcohol is carbonylated in the presence of a carbonylation catalyst to form a carboxylic acid at elevated pressure and temperature. The flash vessel 120 is a tank or vessel in which a reaction mixture obtained in the reactor, for example the reactor 110, is at least partially depressurized and/or cooled to foul) a vapor stream and a liquid stream.

The light-ends area 104 may include a separation column, for example, a light-ends column 130, equipment associated with light-ends column 130, and streams associated with the light-ends column 130. For example, the light-ends area 104 may include light-ends column 130, a decanter 134, and streams 126, 131, 132, 133, 135, 136, 138, 139 and 160. The light-ends column 130 is a fractioning or distillation column and includes any equipment associated with the column, including but not limited to heat exchangers, decanters, pumps, compressors, valves, and the like.

The purification area 106 may include a drying column 140, optionally, a heavy-ends column 150, equipment associated with drying column 140 and heavy-ends column 150, and streams associated with the drying column 140 and heavy-ends column 150. For example, the purification area 106 may include drying column 140, heavy-ends column 150 and streams 136, 141, 142, 145, 148, 151, 152 and 156. The heavy-ends column 150 is a fractioning or distillation column and includes any equipment associated with the column, including but not limited to heat exchangers, decanters, pumps, compressors and valves.

The recycle area 108 may include process streams recycled to the reaction area 102 and/or light-ends area 104. For example, in FIG. 1, the recycle area 108 may include streams 121, 138, 139 and 148.

In one or more embodiments, the reactor 110 may be configured to receive a carbon monoxide feed stream 114 and a methanol or methanol/methyl acetate feed stream 112. A reaction mixture may be withdrawn from the reactor in stream 111. Other streams may be included, for example, a stream that may recycle a bottoms mixture of the reactor 110 back into the reactor 110, or a stream may be included to release a gas from the reactor 110. Stream 111 may include at least a part of the reaction mixture.

In one or more embodiments, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In one or more embodiments, stream 126 may include acetic acid, water, methyl iodide, methyl acetate, HI, and mixtures thereof, for example.

In an embodiment, the light-ends column 130 may include a distillation column and equipment associated with the distillation column including but not limited to a heat exchanger 137, a decanter 134, pumps, compressors, valves, and other related equipment. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus be considered in the recycle area 108, in the light-ends area 104, and in the reactor area 102). Stream 136 may emit from the light-ends column 130. Other streams may be included, for example, a stream that may recycle a bottoms mixture of the light-ends column 130 back into the light-ends column 130. Any stream received by or emitted from the light-ends column 130 may pass through a pump, compressor, heat exchanger, and the like as is common in the relevant art.

In some embodiments, the drying column 140 may comprise a vessel and equipment associated with the vessel including but not limited to heat exchangers, decanters, pumps, compressors, valves, and the like. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment that is readily available, for example, a heat exchanger or separation vessel before streams 145 or 148 recycle components of stream 142. Other streams may be included, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may include acetic acid product.

The purification area 106 may further include an adsorption bed 200. A variety of the streams may be passed therethrough prior to proceeding downstream. For example, stream 156 may be passed through the adsorption bed 200 via stream 156a to form stream 156b. Alternatively, or combination therewith, stream 152 may be passed through the adsorption bed 200 via stream 152a to form stream 152b. Alternatively, or combination therewith, stream 138 may be passed through the adsorption bed 200 via stream 138a to form stream 138b. Alternatively, or combination therewith, stream 141 may be passed through the adsorption bed 200 via stream 141a to form stream 141b.

Alternative embodiments for the carboxylic acid production system 100 may be found in U.S. Pat. No. 6,552,221, which is incorporated herein by reference.

EXAMPLES

To facilitate a better understanding of the disclosure, the following examples of embodiments are given. In no way should the following examples be read to limit, or to define, the scope of the appended claims.

Comparative Example 1

Figure 2:
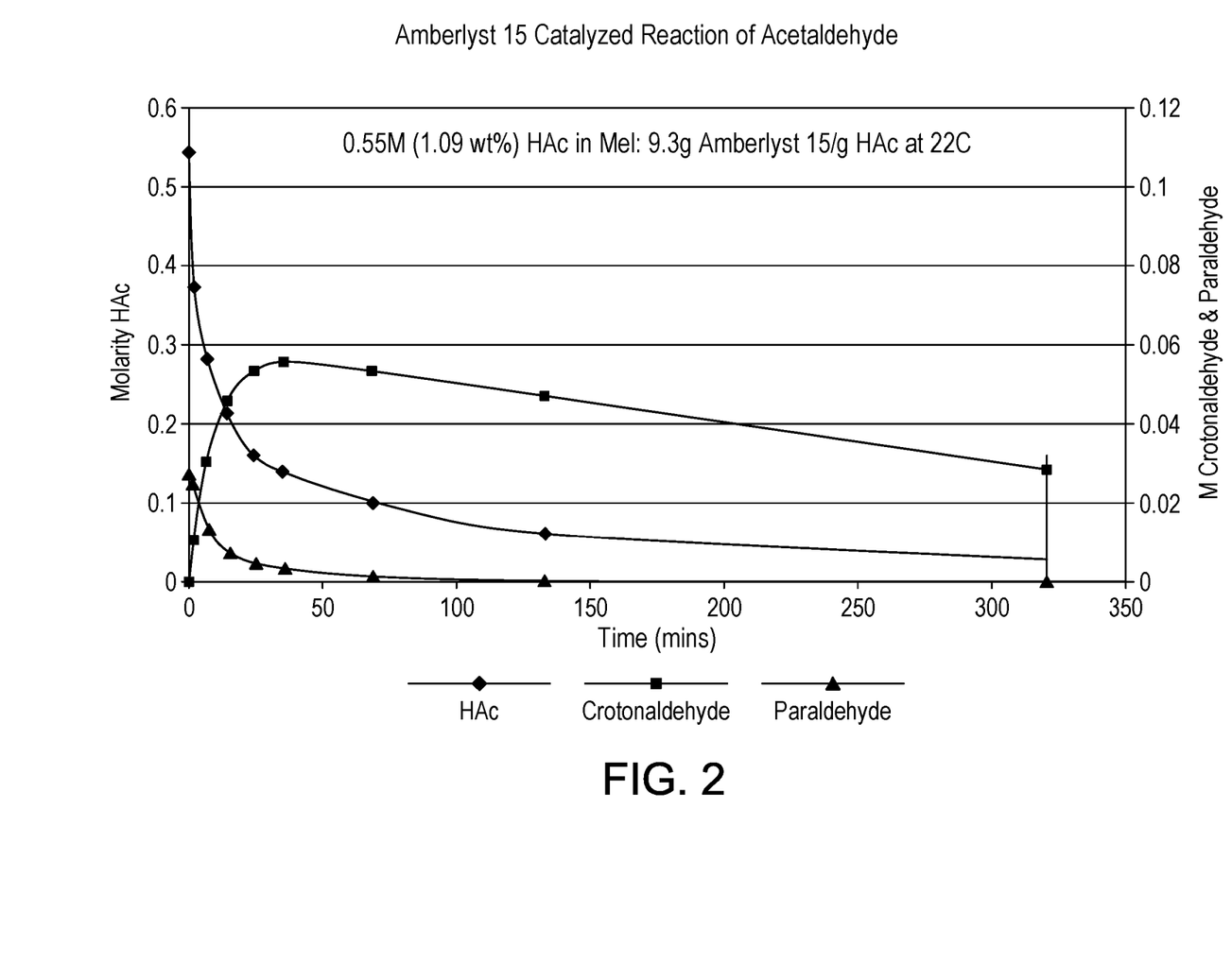
FIG. 2 illustrates a plot of the concentration of various components in a solution when contacted with Amberlyst® 15.

Previous studies to separate impurities, including acetaldehyde, from acetic acid formed in carbonylation processes have included a carbonylation product stream with Amberlyst® 15, a commercially available polymeric resin based on crosslinked styrene divinyl benzene copolymers. Studies were undertaken to determine the catalytic and/or adsorption activity of Amberlyst® 15 with reference to contact with acetaldehyde. The conditions of such studies are illustrated in FIG. 2. It was observed that Amberlyst® 15 catalyzes an initial rapid kinetically controlled and reversible oligomerization of acetaldehyde to trimeric paraldehyde. This was followed by a slower, thermodynamically controlled aldol condensation of acetaldehyde to crotonaldehyde as shown in FIG. 2. It is to be noted that in FIG. 2, that depending on the conditions, particularly temperature, crotonaldehyde may be slowly directly adsorbed or reactively adsorbed on the resin. Thus, depending on the conditions, the resin acted in catalyst only mode or in catalyst and adsorbent mode. In either case, large quantities of a species (e.g., crotonaldehyde) that was not typically present in the process (other than at ppm levels) were formed.

Example 1

Figure 3:
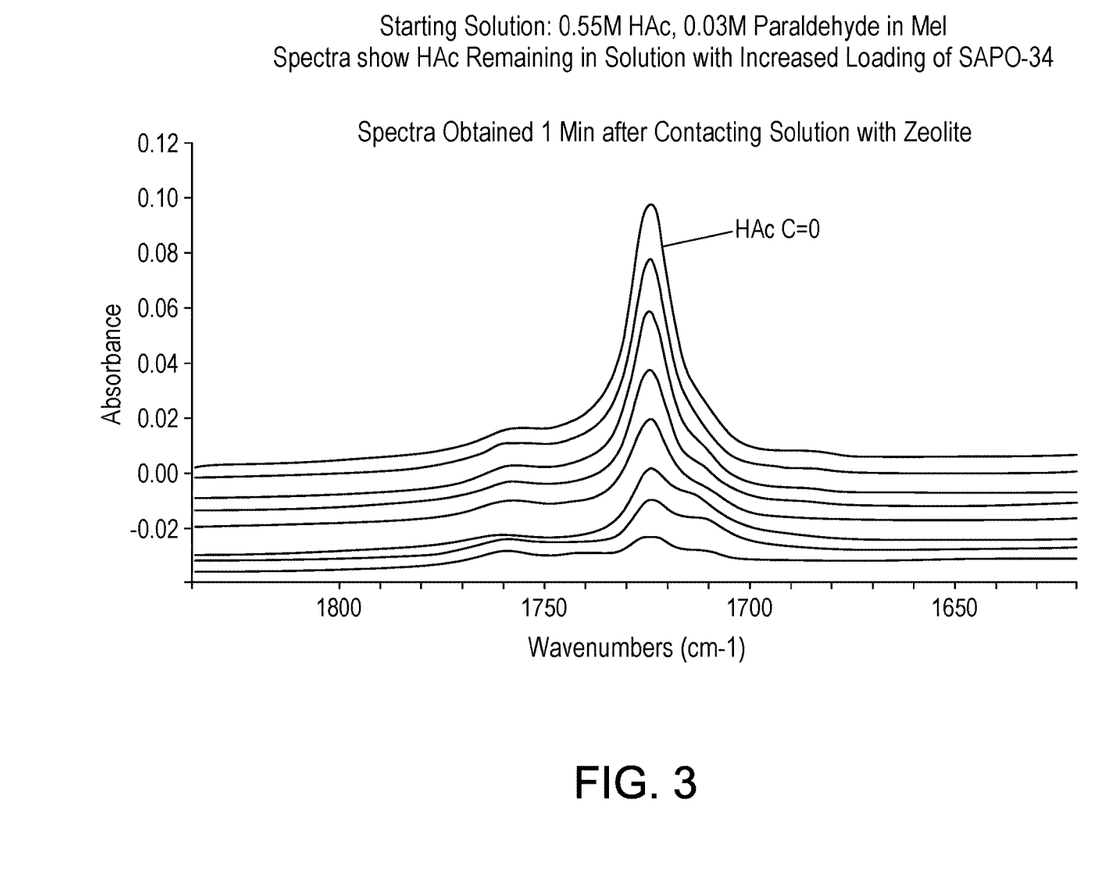
FIG. 3 illustrates FTIR spectroscopic analysis of acetaldehyde in SAPO-34 mixtures under various conditions.

Studies were undertaken to determine the catalytic and/or adsorption activity of various acidic zeolites with reference to contact with acetaldehyde. To separate vials containing similar volumes of a stock solution of acetaldehyde in methyl iodide (MeI) solvent, variable quantities of SAPO-34 were added to each vial and at one minute post addition, each slurry was sampled for Fourier transform infrared spectroscopy (FTIR) analysis. Subsequent sampling indicated that any reaction that takes place is nearly complete after one minute. Overlaid spectra in FIG. 3 show the carbonyl peak of acetaldehyde in the various slurries at one minute post addition with decreasing peak intensity being associated with increased quantities of SAPO-34. It should be noted that the stock solution contained a small amount of paraldehyde, which forms over time via oligomerization in MeI even without any acid catalyst present.

Figure 4:
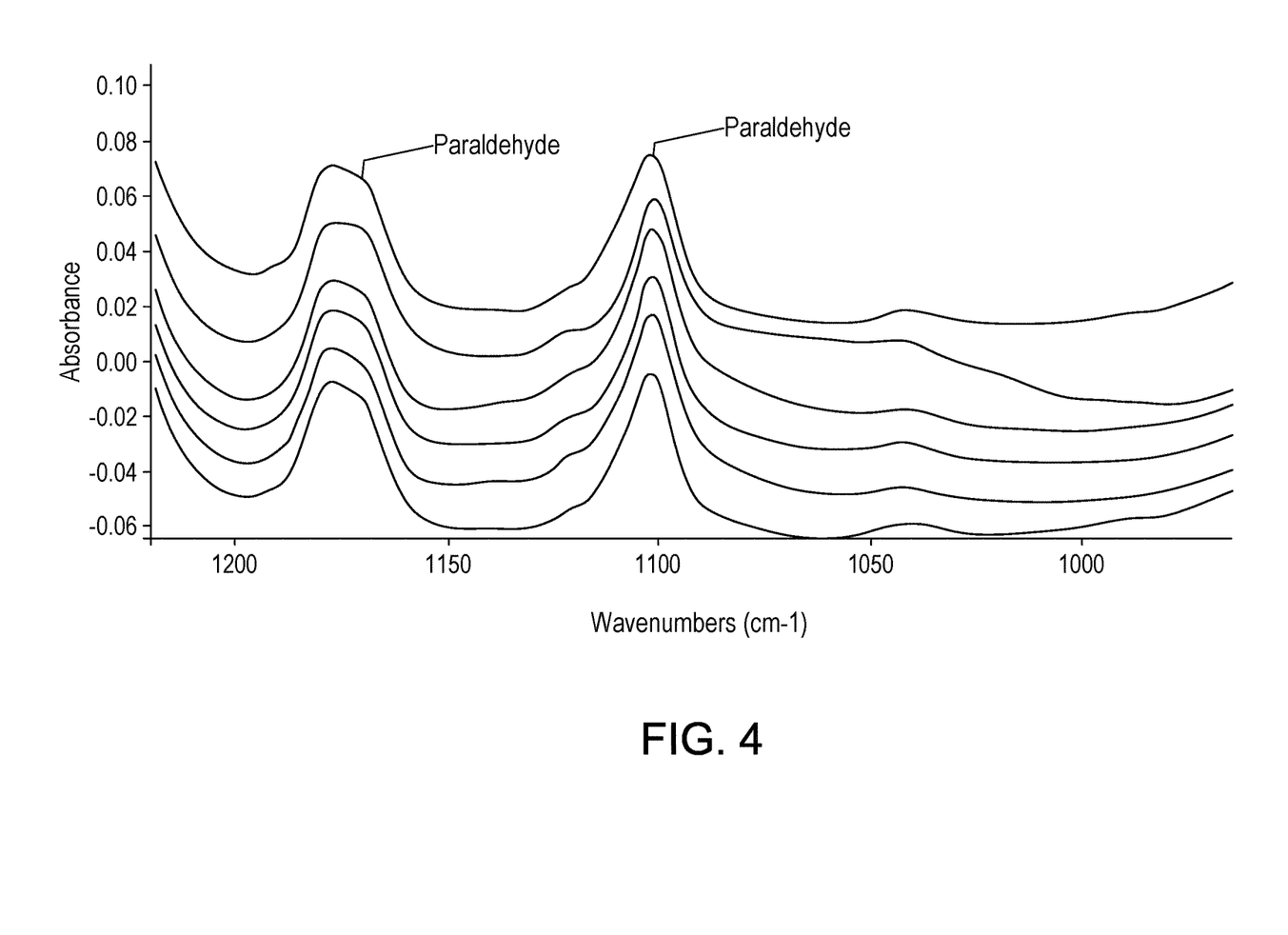
FIG. 4 illustrates FTIR spectroscopic analysis of paraldehyde in SAPO-34 mixtures under various conditions.

FIG. 4 illustrates a similar overlaid profile except in this case, the spectral region shows the paraldehyde peaks that were present in stock solution prior to contact with SAPO-34. No change in paraldehyde concentration is observed regardless of SAPO-34 loading. In addition, no peak for crotonaldehyde and no other new peaks were observed in solution, leading to the conclusion that the acetaldehyde was directly adsorbed or reactively adsorbed on the SAPO-34.

Figure 5:
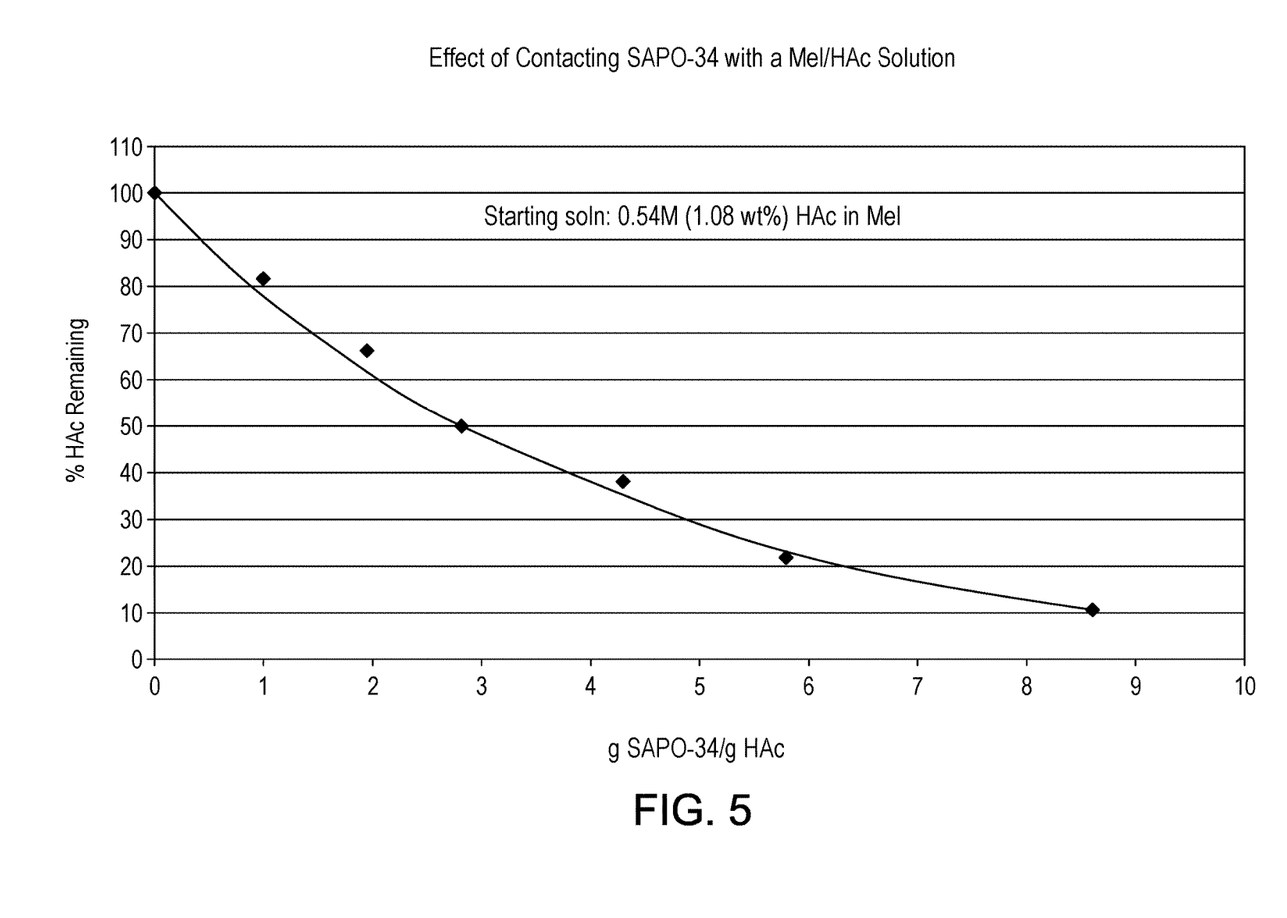
FIG. 5 illustrates a plot of the percentage of impurity removal at various loadings of SAPO-34.

FIG. 5 illustrates the percentage of acetaldehyde (HAc) remaining in solution as a function of SAPO-34 loading. For such illustration, a fresh stock solution of HAc/MeI was prepared in which no paraldehyde was present and none was observed to form during contact of stock solution with SAPO-34.

Example 2

Figure 6:
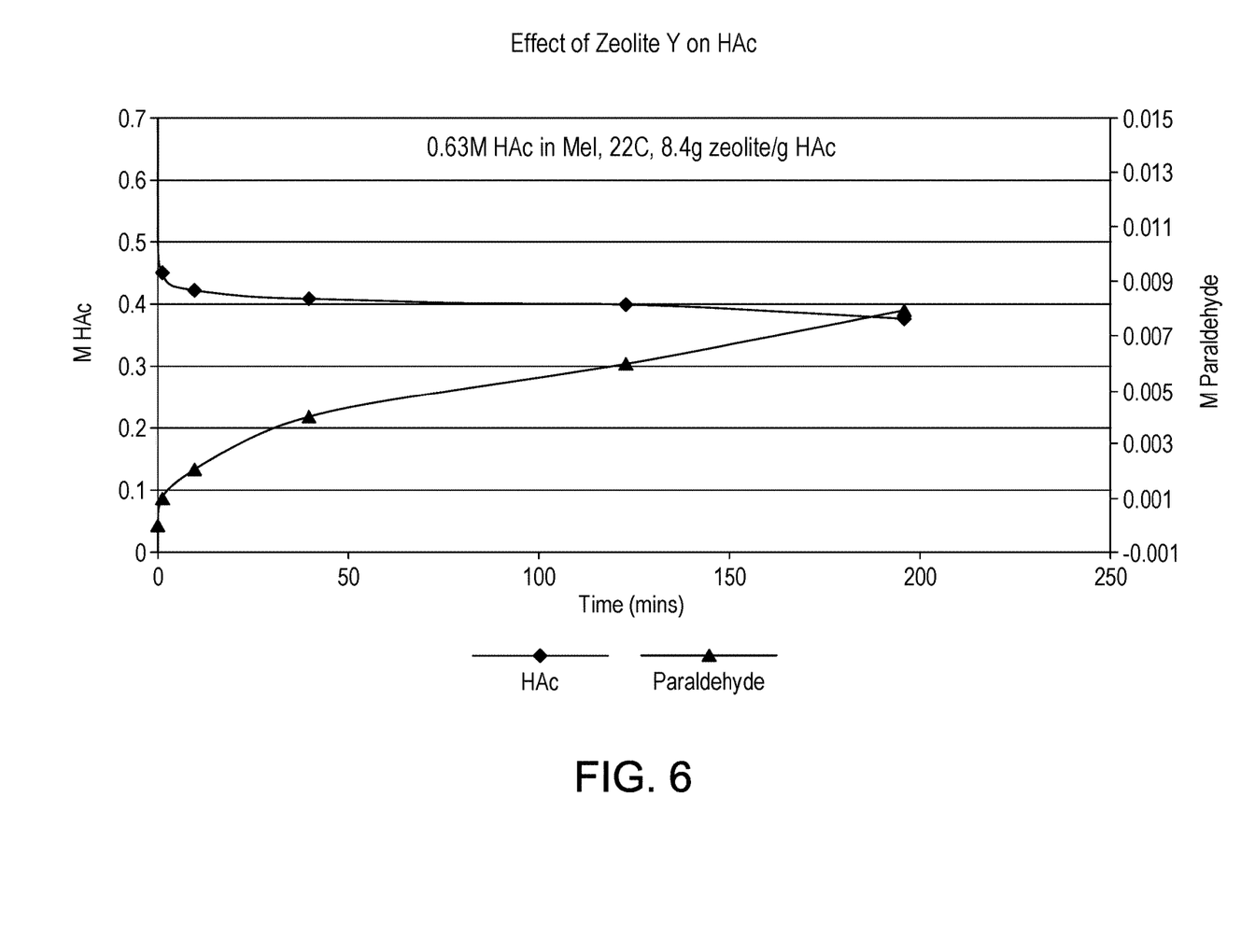
FIG. 6 illustrates a plot of the percentage of impurity removal at various times for a comparison adsorbent.

A time profile for a similar experiment carried out with a fresh stock solution and with zeolite Y (an acidic aluminosilicate) is illustrated in FIG. 6. Such illustration indicates that there was no rapid adsorption of acetaldehyde and only a slow oligomerization to paraldehyde. Similar behavior was observed with other aluminosilicates as shown in Table 1.

TABLE 1

| Zeolite | Loading (per g HAc) | Initial HAc, M | 1 min, HAc, M |
|---|---|---|---|
| ZSM-H 371 | 8.5 | 0.55 | 0.41 |
| ZSM-H 26 | 8.4 | 0.55 | 0.44 |
| SAPO-34 | 8.4 | 0.55 | 0.06 |

*Note:
Testing conditions: 0.55M (1.09 wt. %) HAc in MeI, 22° C.

Example 3

Figure 7:
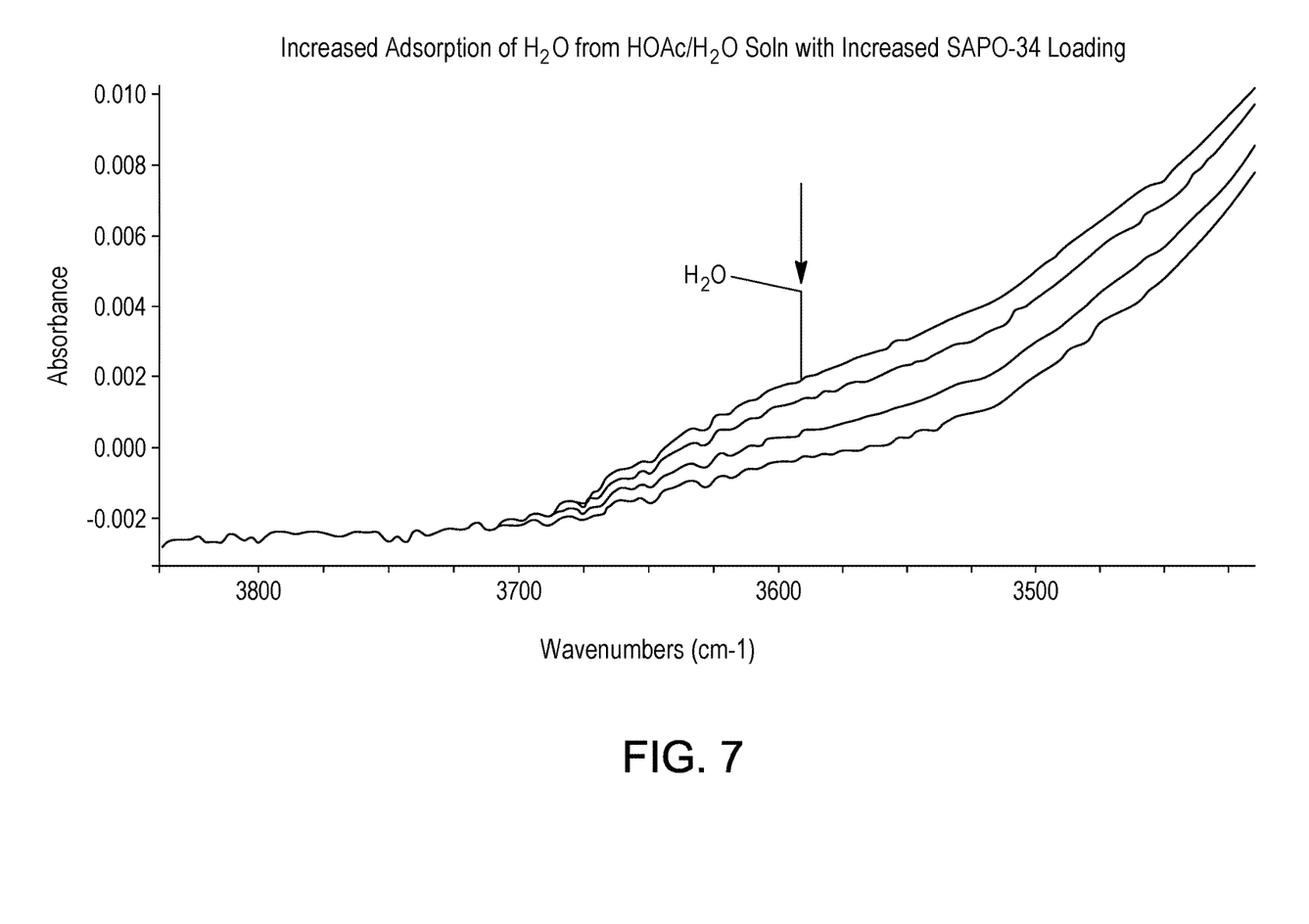
FIG. 7 illustrates FTIR spectroscopic analysis of $H_2O$ in SAPO-34 mixtures under various conditions.

Slurries with different SAPO-34 loading were prepared in which the slurries included solutions of 1.81 wt. % water in HOAc. The slurries were all sampled at the one minute point for analysis and the spectra in FIG. 7 show that there is decreasing water concentration in solution as SAPO-34 loading increases. Thus, it has been found that SAPO-34 can selectively adsorb water from a solution of acetic acid.

To demonstrate that this adsorption effect is unique, a number of other adsorbent materials were investigated and are shown in Table 2. Data for SAPO-11 appear to show the reverse effect for that observed for SAPO-34. Increased loading of SAPO-11 led to an increased solution water concentration and associated decreased HOAc concentration.

TABLE 2

| Adsorbent | Loading | $H_2O$, wt. % | HOAc, wt. % | Material Balance |
|---|---|---|---|---|
| None | N/A | 1.81 | 98.19 | 100 |
| SAPO-34 | 2.88 | 1.51 | 98.48 | 99.99 |
| SAPO-34 | 6.31 | 1.00 | 98.90 | 99.90 |
| SAPO-34 | 13.96 | 0.66 | 99.23 | 99.89 |
| SAPO-34 | 21.80 | 0.66 | 99.23 | 99.89 |
| SAPO-11 | 3.36 | 1.96 | 97.99 | 99.95 |
| SAPO-11 | 6.77 | 2.03 | 97.87 | 99.90 |
| SAPO-11 | 14.04 | 2.13 | 97.75 | 99.88 |
| NaY Zeolite | 4.32 | 2.01 | 97.95 | 99.96 |
| NaY Zeolite | 6.92 | 1.77 | 98.16 | 99.93 |
| NaY Zeolite | 14.58 | 1.64 | 98.23 | 99.87 |
| SAPO-05 | 13.80 | 1.85 | 98.16 | 100.01 |

Example 4

Figure 8:
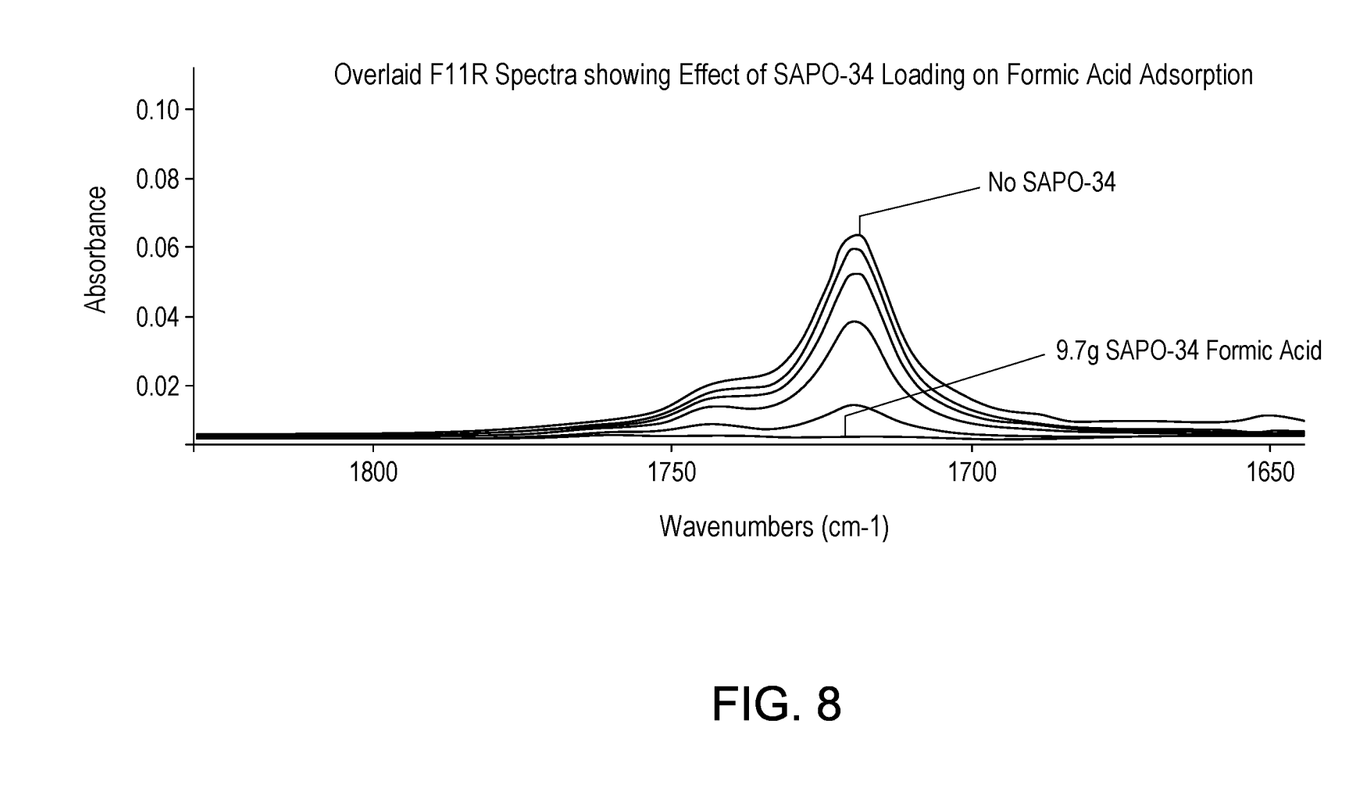
FIG. 8 illustrates FUR spectroscopic analysis of formic acid in SAPO-34 mixtures under various conditions.
Figure 9:
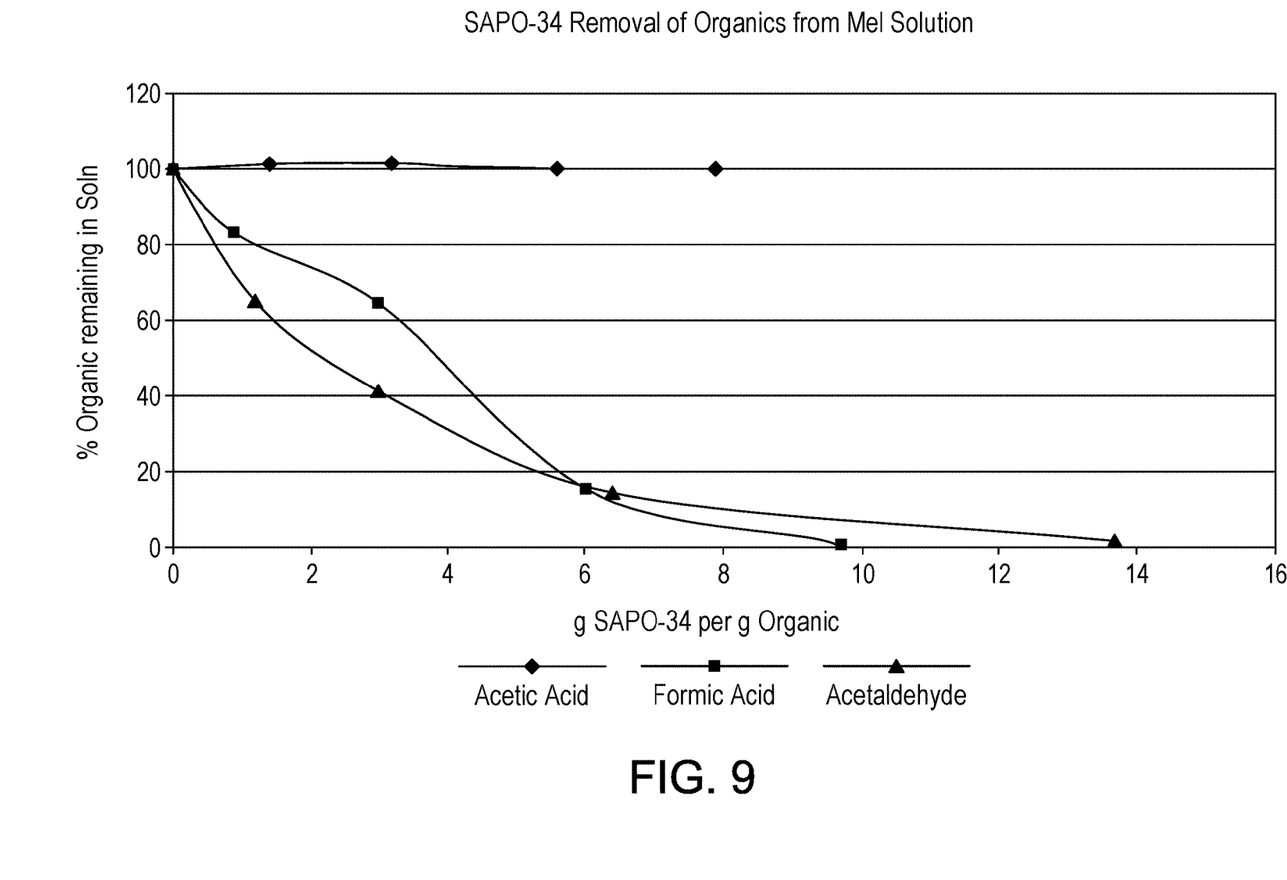
FIG. 9 illustrates a plot of the percentage of impurity removal at various loadings of SAPO-34.

Slurries with different SAPO-34 loading were prepared in which the slurries included fixed volumes of a formic acid solution in methyl iodide solvent. Spectra were obtained by sampling the slurries one minute after mixing. Increased loading of SAPO-34 relative to formic acid led to complete disappearance of formic acid from solution (see, FIG. 8). In contrast, similar experiments with an acetic acid solution in methyl iodide solvent showed that 100% of the acetic acid remained in solution (see, FIG. 9). The slurries were all sampled at the one minute point for analysis and the spectra in FIG. 7 show that there is decreasing water concentration in solution as SAPO-34 loading increases. Thus, it has been found that SAPO-34 can selectively adsorb water from a solution of acetic acid.

Figure 10:
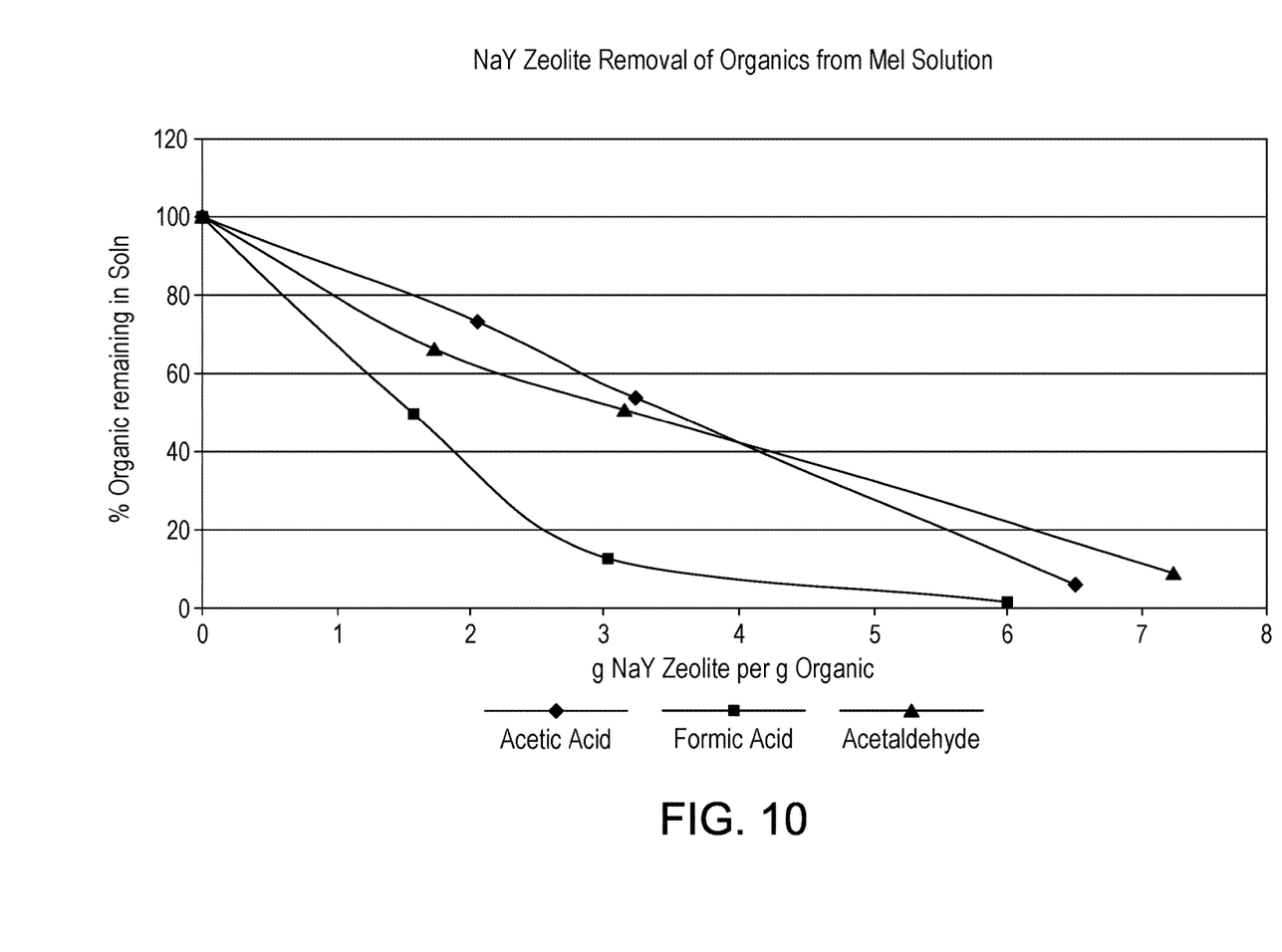
FIG. 10 illustrates a plot of the percentage of impurity removal at various loadings of a comparison adsorbent.

To further demonstrate the surprising nature of these findings, similar loading experiments were carried out with NaY zeolite as the adsorbent. The plot in FIG. 10 shows that NaY zeolite has no size exclusion capability to selectively adsorb either formic acid or acetaldehyde from acetic acid.

To demonstrate that commercial SAPO materials do not have universally similar size exclusion capabilities, adsorption experiments were carried out with a variety of adsorbents. The data in Table 3 compares the adsorption ability of the adsorbents and organics tested at an approximately similar fixed loading. The data are based on FTIR spectra obtained one minute after slurry preparation.

TABLE 3

| Organic | Adsorbent | Loading | % Removal |
|---|---|---|---|
| Acetaldehyde | SAPO-34 | 6.4 | 86 |
| Acetaldehyde | SAPO-11 | 6.1 | 0 |
| Acetaldehyde | SAPO-05 | 6.6 | 6.7 |
| Acetaldehyde | NaY Zeolite | 7.3 | 93.4 |
| Formic Acid | SAPO-34 | 6.0 | 84.8 |
| Formic Acid | SAPO-11 | 6.0 | 71.5 |
| Formic Acid | SAPO-05 | 6.1 | 34.3 |
| Formic Acid | NaY Zeolite | 6.1 | 98.2 |
| Acetic Acid | SAPO-34 | 5.6 | 0 |
| Acetic Acid | SAPO-11 | 6.8 | 18.7 |
| Acetic Acid | SAPO-05 | 7.1 | 6.5 |
| Acetic Acid | NaY Zeolite | 6.6 | 93.4 |

*Note:
Loading was measured as g adsorbent/g organic

What is claimed is:

1. A process for the production of acetic acid comprising: contacting methanol and carbon monoxide in the presence of a liquid reaction medium under carbonylation conditions sufficient to form a carbonylation product comprising acetic acid and one or more components selected from acetaldehyde, formic acid and combinations thereof, wherein the liquid reaction medium comprises:
   a carbonylation catalyst selected from rhodium catalysts, iridium catalysts and palladium catalysts; and
   water at a concentration in a range of 1-14 wt. %, based on the total weight of the liquid reaction medium; and
   contacting at least a portion of the carbonylation product with a silicoaluminophosphate (SAPO) adsorbent comprising an average surface area of at least 500 m²/g at adsorption conditions sufficient to selectively reduce a concentration of one or more components present in the carbonylation product.

2. The process of claim 1, wherein the adsorbent is represented by the formula $(SiO_2)_x(Al_2O_3)_y(P_2O_5)_z$, wherein $x\pm y+z=1$.

3. The process of claim 1, wherein the adsorbent comprises a micro-porous material.

4. The process of claim 1, wherein the adsorbent comprises an average pore volume of at least 0.23 cm³/g.

5. The process of claim 1, wherein the adsorbent is disposed on a fixed bed and the at least a portion of the carbonylation product stream passes through the bed to selectively reduce the concentration of the one or more components.

6. The process of claim 1, wherein the adsorbent is loaded on the fixed bed at a level sufficient to provide a loading of from 1 to 10 g adsorbent/g component to be selectively adsorbed.

7. The process of claim 1, wherein the adsorption conditions comprise an adsorption temperature in a range of room temperature to 250° C.

8. The process of claim 1, wherein the at least a portion of the carbonylation product comprises acetaldehyde, formic acid or a combination thereof and less than 1 wt. % water.

9. The process of claim 8, wherein a concentration of acetaldehyde is selectively reduced by at least 80%.

10. The process of claim 8, wherein acetaldehyde is selectively reduced to provide a purified acetic acid stream comprising an acetaldehyde concentration of less than 2 wt. % based on the total weight of the purified acetic acid stream.

11. The process of claim 8, wherein a concentration of formic acid is selectively reduced by at least 80%.

12. The process of claim 8, wherein formic acid is selectively reduced to provide a purified acetic acid stream comprising a formic acid concentration of less than 2 wt. % based on the total weight of the purified acetic acid stream.

13. The process of claim 1, wherein the at least a portion of the carbonylation product comprises water at a concentration of at least 200 ppm based on the total weight of the carbonylation product.

14. The process of claim 13, wherein a concentration of water present in the at least a portion of the carbonylation product stream is selectively reduced by at least 50%.

15. The process of claim 13, wherein water is selectively reduced to provide a purified acetic acid stream comprising a water concentration of less than 1 wt. % based on the total weight of the purified acetic acid stream.

16. The process of claim 1, wherein the adsorbent comprises a three-dimensional framework of cages interconnected by windows.

17. The process of claim 16, wherein the adsorbent comprises an average cage diameter of 4-12 angstroms and an average window diameter of 2-6 angstroms.

18. The process of claim 1, wherein the adsorbent is capable of undergoing regeneration.

19. The process of claim 2, wherein the adsorbent is capable of undergoing regeneration.

* * * * *

UNITED STATES PATENT AND TRADEMARK OFFICE
CERTIFICATE OF CORRECTION

| | | |
|---|---|---|
| PATENT NO. | : 9,873,655 B2 | Page 1 of 1 |
| APPLICATION NO. | : 15/367999 | |
| DATED | : January 23, 2018 | |
| INVENTOR(S) | : Hallinan et al. | |

It is certified that error appears in the above-identified patent and that said Letters Patent is hereby corrected as shown below:

In the Specification

In Column 3, Line 26, delete "FUR", and insert -- FTIR --

In Column 7, Line 12, delete "aluminophsophate", and insert -- aluminophosphate --

In Column 7, Line 24, delete "a", and insert -- an --

In Column 9, Line 26, delete "foul)", and insert -- form --

In Column 11, Line 8, delete "bed.", and insert -- bed --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*